US006090960A

United States Patent [19]
Senzaki et al.

[11] Patent Number: 6,090,960
[45] Date of Patent: Jul. 18, 2000

[54] PRECURSOR WITH (METHOXY) (METHYL) SILYLOLEFIN LIGAND TO DEPOSIT COPPER AND METHOD SAME

[75] Inventors: Yoshihide Senzaki; Lawrence J. Charneski; Masato Kobayashi; Tue Nguyen, all of Vancouver, Wash.

[73] Assignees: Sharp Laboratories of America, Inc., Camas, Wash.; Sharp Kabushiki Kaisha, Osaka, Japan

[21] Appl. No.: 08/779,640

[22] Filed: Jan. 7, 1997

[51] Int. Cl.[7] .................................. C07F 7/08; C07F 1/08
[52] U.S. Cl. ............................. 556/9; 556/10; 427/248.1; 427/250; 427/252; 106/1.26
[58] Field of Search ........................ 556/9, 10; 427/268.1, 427/250, 252; 106/1.26

[56] References Cited

U.S. PATENT DOCUMENTS

| | | | |
|---|---|---|---|
| 5,028,724 | 7/1991 | Ivankovits et al. | 556/40 |
| 5,085,731 | 2/1992 | Norman et al. | 156/646 |
| 5,096,737 | 3/1992 | Baum et al. | 427/38 |
| 5,098,516 | 3/1992 | Norman et al. | 156/666 |
| 5,144,049 | 9/1992 | Norman et al. | 556/12 |
| 5,187,300 | 2/1993 | Norman | 556/12 |
| 5,322,712 | 6/1994 | Norman et al. | 427/250 |
| 5,767,301 | 6/1998 | Senzaki et al. | 556/9 |

OTHER PUBLICATIONS

Article entitled, "Chemical Additives for Improved Copper Chemical Vapour Deposition Processing" by J. Norman, D. Roberts, A. Hochberg, R. Smith, G. Petersen, J. Parmeter, C. Apblett, T. Omstead in the Thin Solid Films 262 (1995) pp. 46–51.

Article entitled, "MOCVD of Copper from New and Liquid Precursors (hfac)CuL, Where L = 1–Pentene, ARMS, and VTMOS", by H.K. Shin, H.J. Shin, S.J. Lim, D.J. Yoo, N.Y. Oh, H.J. Yoo, J.T.Baek, C.H. Jun, & Y.T. Kim in the Material Res. Soc. Symp. Proc. vol. 427, 1996 Materials Research Society, pp. 219–223.

Article entitled, "Ligand–Stabilized Copper (I) Hexafluoracetylacetonate Complexes: NMR Spectroscopy and the Nature of the Copper–Alkene Bond" by T. Baum, C. Larson and G. May, published in Journal of Organometallic Chemistry, 425 (1992) pp. 189–200.

Article entitled, "The Effect of Adding Hexafluoracetylacetone on Chemical Vapor Deposition of Copper Using cu(I) and Cu(II) Precursor Systems", by N. Awaya, K. Ohno and Y. Arita, published in J. Electrochem. Soc. vol. 142, No. 9, Sep. 1995, pp. 3173–3179.

Article entitled, Chemical Vapor Deposition of Copper from Hexafluoracetylacetonato Copper(I) Vinyltrimethylsilane, Deposition Rates, Mehaism, Selectivity, Morphology & Resistivity as a Function of Temperature and Pressure by A. Jain, K.M. Chi, T.T. Kodas & M.J. Hampden–Smith, published in J. Electrochem Soc. vol. 140, No. 5, May 1993, pp. 1434–1439.

Article Entitled, Chemical Additives for Improved Copper CVD Processing Using (hfac) Cu(TMVS) by A. Hochberg, J. Norman and D. Roberts, published in Conference Proceedings ULSI–X, 1995 Materials Reserach Society, pp. 79–86.

*Primary Examiner*—Paul F. Shaver
*Attorney, Agent, or Firm*—Gerald Maliszewski

[57] ABSTRACT

A method of applying chemical vapor deposition (CVD) copper (Cu) to integrated circuit substrates using a precursor with either a dimethoxymethylvinylsilane (dmomvs), or methoxydimethylvinylsilane (modmvs), silylolefin ligand bonded to (hfac)Cu is provided. The dmomvs ligand is able to provide the electrons of oxygen atoms from two methoxy groups to improve the bond between the ligand and the (hfac)Cu complex. The improved bond helps insure that the ligand separates from the (hfac)Cu complex at consistent temperatures when Cu is to be deposited. In situations where a precursor having a smaller molecular weight is desired, the modmvs ligand is used to provide electrons from the oxygen atom of the single methoxy group. In the preferred embodiment, water vapor is added to the volatile precursor to improve the conductivity of the deposited Cu. Other embodiments provide a precursor blend made from additional silylolefins, hexafluoroacetylacetone (H-hfac), and water, either separately, or in combinations, to enhance deposition rate, conductivity, and precursor stability. A Cu precursor compound including the dmomvs and modmvs ligands with (hfac)Cu is also provided.

30 Claims, 4 Drawing Sheets

PRECURSOR WITH (METHOXY) (METHYL) SILYLOLEFIN LIGAND TO DEPOSIT COPPER AND METHOD SAME

BACKGROUND AND SUMMARY OF THE INVENTION

This invention relates generally to integrated circuit processes and fabrication, and more particularly, to a precursor and method, having enhanced temperature stability, used to deposited copper on selected integrated circuit surfaces.

The demand for progressively smaller, less expensive, and more powerful electronic products, in turn, fuels the need for smaller geometry integrated circuits (ICs) on larger substrates. It also creates a demand for a denser packaging of circuits onto IC substrates. The desire for smaller geometry IC circuits requires that the interconnections between components and dielectric layers be as small as possible. Therefore, research continues into reducing the width of via interconnects and connecting lines. The conductivity of the interconnects is reduced as the area of the interconnecting surfaces is reduced, and the resulting increase in interconnect resistivity has become an obstacle in IC design. Conductors having high resistivity create conduction paths with high impedance and large propagation delays. These problems result in unreliable signal timing, unreliable voltage levels, and lengthy signal delays between components in the IC. Propagation discontinuities also result from intersecting conduction surfaces that are poorly connected, or from the joining of conductors having highly different impedance characteristics.

There is a need for interconnects and vias to have both low resistivity, and the ability to withstand process environments of volatile ingredients. Aluminum and tungsten metals are often used in the production of integrated circuits for making interconnections or vias between electrically active areas. These metals are popular because they are easy to use in a production environment, unlike copper which requires special handling.

Copper (Cu) would appear to be a natural choice to replace aluminum in the effort to reduce the size of lines and vias in an electrical circuit. The conductivity of copper is approximately twice that of aluminum and over three times that of tungsten. As a result, the same current can be carried through a copper line having nearly half the width of an aluminum line.

The electromigration characteristics of copper are also much superior to those of aluminum. Aluminum is approximately ten times more susceptible than copper to degradation and breakage due to electromigration. As a result, a copper line, even one having a much smaller cross-section than an aluminum line, is better able to maintain electrical integrity.

There have been problems associated with the use of copper, however, in IC processing. Copper pollutes many of the materials used in IC processes and, therefore barriers are typically erected to prevent copper from migrating. Elements of copper migrating into these semiconductor regions can dramatically alter the conduction characteristics of associated transistors. Another problem with the use of copper is the relatively high temperature needed to deposit it on, or removing it from, an IC surface. These high temperatures can damage associated IC structures and photoresist masks.

It is also a problem to deposit copper onto a substrate, or in a via hole, using the conventional processes for the deposition of aluminum when the geometries of the selected IC features are small. That is, new deposition processes have been developed for use with copper, instead of aluminum, in the lines and interconnects of an IC interlevel dielectric. It is impractical to sputter metal, either aluminum or copper, to fill small diameter vias, since the gap filling capability is poor. To deposit copper, first, a physical vapor deposition (PVD), and then, a chemical vapor deposition (CVD) technique, have been developed by the industry.

With the PVD technique, an IC surface is exposed to a copper vapor, and copper is caused to condense on the surfaces. The technique is not selective with regard to surfaces. When copper is to be deposited on a metallic surface, adjoining non-conductive surfaces must either be masked or etched clean in a subsequent process step. As mentioned earlier, photoresist masks and some other adjoining IC structures are potentially damaged at the high temperatures at which copper is processed. The CVD technique is an improvement over PVD because it is more selective as to which surfaces copper is deposited on. The CVD technique is selective because it is designed to rely on a chemical reaction between the metallic surface and the copper vapor to cause the deposition of copper on the metallic surface.

In a typical CVD process, copper is combined with a ligand, or organic compound, to help insure that the copper compound becomes volatile, and eventually decomposes, at consistent temperatures. That is, copper becomes an element in a compound that is vaporized into a gas, and later deposited as a solid when the gas decomposes. Selected surfaces of an integrated circuit, such as diffusion barrier material, are exposed to the copper gas, or precursor, in an elevated temperature environment. When the copper gas compound decomposes, copper is left behind on the selected surface. Several copper gas compounds are available for use with the CVD process. It is generally accepted that the configuration of the copper gas compound, at least partially, affects the ability of the copper to be deposited on to the selected surface.

$Cu^{+2}(hfac)_2$, or copper (II) hexafluoroacetylacetonate, precursors have previously been used to apply CVD copper to IC substrates and surfaces. However, these $Cu^{+2}$ precursors are notable for leaving contaminates in the deposited copper, and for the relatively high temperatures that must be used to decompose the precursor into copper. Currently, more success has been found with the use of $Cu^{+1}(hfac)$ compounds to apply copper. Norman, et al., U.S. Pat. No. 5,322,712, discloses a (hfac)Cu(tmvs), or copper hexafluoroacetylacetonate trimethylvinylsilane, precursor that is the industry standard at the time of this writing. Alternately, tmvs is known as vtms, or vinyltrimethylsilane. This precursor is useful because it can be used at relatively low temperatures, approximately 200° C. In addition, the film resisitivity of copper applied with this method is very good, approaching the physical limit of $1.7\mu\Omega$-cm. However, the adhesiveness between copper deposited with this precursor and the surface to which it is deposited is not always good. Also, the precursor is not especially stable, and can have a relatively short shelf life if not refrigerated. Various ingredients have been added to (hfac)Cu(tmvs) to improve its adhesiveness, temperature stability, and the rate at which it can be deposited on an IC surface. A co-pending application Ser. No. 08/745,652 filed Nov. 8, 1996, entitled "Cu(hfac) TMVS Precursor With Water Additive To Increase The Conductivity Of Cu And Method For Same", invented by Nguyen et al., Attorney Docket No. SMT 244, a assigned to the same assignee as the instant patent, discloses and precursor and method of improving the electrical conductivity of Cu deposited with (hfac)Cu(tmvs).

It is generally acknowledged in the industry that (hfac) Cu(tmvs) becomes unstable, and begins to decompose, above 35° C. Use of a (hfac)Cu(tmvs) precursor stored at this temperature leads to undesirable process results. Typically, the precursor is a liquid at room temperature, and must be converted to a vapor form. In interacting with a heated target surface, the vaporized precursor first cleaves the tmvs ligand, and then the hfac, leaving Cu on the target surface. During this process a disproportionation reaction occurs in which uncharged atoms of Cu are left on the surface, while volatile forms of $Cu^{+2}(hfac)_2$ and the tmvs ligand are exhausted through the system.

As an unstable precursor is heated to a vapor, the tmvs ligand cleaves unevenly from the precursor, some cleavage, or decomposition, occurs at low temperature, and some at higher temperatures. Because the precursor decomposes at low temperatures, the precursor vacuum pressure, or partial pressure, remains undesirably low, resulting in low Cu deposition rates, uneven surfaces, and variances in surface conductances. The effectivity of (hfac)Cu(tmvs) stored at temperatures lower than 35° C. is also unpredictable. "Fresh" batch of precursor, or precursor stored at temperatures well below room temperature are used to guarantee predictable processes.

Various additives have been mixed with the (hfac)Cu(tmvs) precursor to improve its temperature stability. It is well known to blend hexafluoroacetylacetone (H-hfac), tmvs, and other chemical agents to improve temperature stability. Baum et al., in "Ligand-stabilized copper(I) hexafluoroacetylacetonate complexes: NMR spectroscope and the nature of the copper-alkene bond", J. Organomet. Chem., 425, 1992, pp. 189–200, disclose alkene groups affecting improvement in the stability of Cu precursors. They also speculate on the nature of sigma and pi bonds in the Cu-alkene bond of a (hfac)Cu(alkene) complex.

Choi et al., in "Chemical vapor deposition of copper with a new metalorganic source", Appl. Phys. Lett. 68 (7), Feb. 12, 1996, pp. 1017–1019, disclose trimethoxyvinylsilane (tmovs) as a ligand to improve the temperature stability of Cu(hfac). Using the tmovs ligand, precursor stability up to the temperature of 70° C. is reported. However, the addition of oxygen atoms to the methyl groups of the ligand is still experimental. That is, the method has not been refined for production environments. There is also concern that a precursor having a heavier molecular weight due to the addition of oxygen atoms to the ligand may yield unexpected premature decomposition problems as higher vaporization temperatures and lower system pressures are required. Further enhancement in the temperature stability of Cu(hfac) precursors is desirable, and the use of other ligands to improve stability remains an area of ongoing research.

It would be advantageous if a method were found of making a Cu(hfac) precursor stable over a wider range of temperatures, and to provide the precursor with a longer shelf life.

It would be advantageous if the ligand attached to the Cu(hfac) precursor would cleave at a consistent temperature. Additionally, it would be advantageous if the alkene ligand and the hfac would cleave at approximately the same temperature to yield consistent precursor decomposition.

It would be advantageous if the temperature at which the (hfac)Cu(ligand) compound decomposes could be increased, thereby increasing the precursor partial pressure, to deposit a thicker layer of copper on selected IC surfaces.

It would also be advantageous if a water additive could be blended with a thermally stable Cu precursor to improve the conductivity, and deposition rate, of the deposited copper.

Accordingly, a volatile Cu precursor compound for the chemical vapor deposition (CVD) of Cu to selected surfaces is provided. The precursor compound comprises $Cu^{+1}$ (hexafluoroacetylacetonate), and a (methoxy)(methyl) silylolefin ligand. That is, the ligand comprises a combination of methyl and methoxy groups, bonded to silicon, which strike a balance between a precursor having the electron donation capability of methoxy in the ligand, and a precursor having a lesser molecular weight due to the methyl in the ligand. The electron donation capability of the oxygen in the (methoxy)(methyl)silylolefin ligand provides a secure bond between the Cu and the (methoxy)(methyl)silylolefin ligand as the compound is heated to vaporization temperature.

In one alternative of the preferred embodiment, the (methoxy)(methyl)silylolefin is dimethoxymethylvinylsilane (dmomvs), whereby the two oxygen atoms of the dimethoxymethyl group donate electrons to Cu to increase the temperature stability of the precursor. In another alternative of the preferred embodiment, the (methoxy)(methyl) silylolefin is methoxydimethylvinylsilane (modmvs), whereby the oxygen atom of the methoxydimethyl group minimally suppresses the precursor volatility. Therefore, a ligand providing electrons from either one, or two, oxygen atoms is disclosed.

The preferred embodiment further includes an addition to the compound to create a precursor blend. The precursor blend further comprises a water vapor having a vacuum partial pressure. The water vapor is blended with the precursor so that the partial pressure of the water vapor is generally in the range of 0.5 to 5% of the precursor partial pressure, whereby the addition of water vapor to the precursor increases the rate of Cu deposition and the electrical conductivity of the deposited Cu.

A method for applying CVD Cu on a selected surface is also provided. The method comprising the steps of: a) exposing each selected Cu-receiving surface to a volatile Cu precursor compound including $Cu^{+1}$ (hexafluoroacetylacetonate) and a (methoxy)(methyl) silylolefin ligand at a predetermined vacuum pressure; and, b) while continuing to carry out step a), depositing Cu on each Cu-receiving surface. The bond between the (methoxy) (methyl)silylolefin ligand and Cu prevents the decomposition of the precursor at low temperatures.

DETAILED DESCRIPTION OF THE PREFERRED EMBODIMENT

Figure 1:
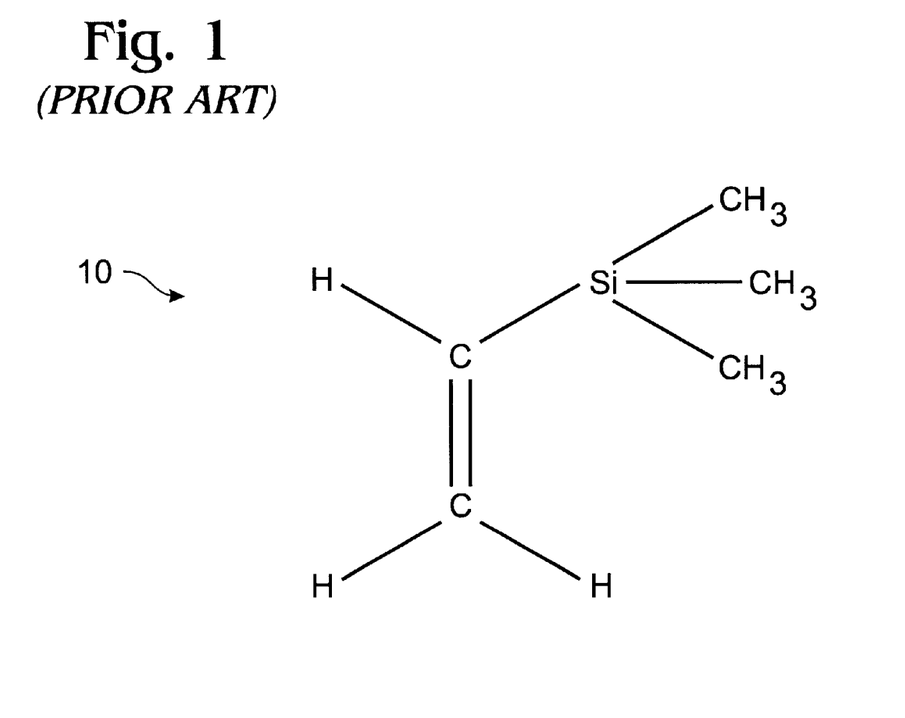
FIG. 1 is a schematic representation of the tmvs ligand (prior art).

FIG. 1 is a schematic representation of the tmvs ligand 10 (prior art). The double lines between the two carbon atoms represent double bonds, while the single lines between the remaining atoms represent, weaker, single bonds. Cu becomes attached to tmvs ligand 10 through the carbon atoms. Cu and hfac form a relatively secure bond, and the resulting $Cu^{+1}(hfac)^{-1}$ complex has no net electrical charge. As is well known in the art, atoms or complexes having opposite charges combine to form very stable complexes. The bonding between the $Cu^{+1}(hfac)^{-1}$ complex, hereafter called Cu(hfac), and ligand 10 is relatively weak due to lack of opposing net charges. For this reason, tmvs ligand 10 is first to cleave from the Cu precursor as it is vaporized and applied to a target surface. While not intending to be bound by theory, it is believed that if the ligand were able to provide more electrons, the bond between the ligand and the Cu(hfac) could be improved, resulting in a Cu precursor with improved temperature stability.

Figure 2:
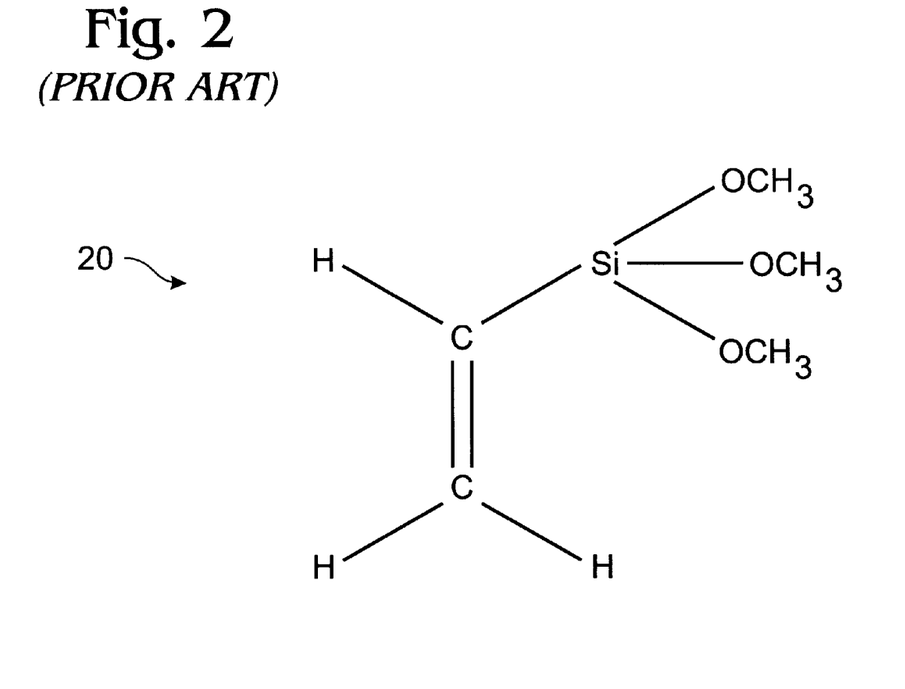
FIG. 2 is a schematic representation of the tmovs ligand (prior art).

FIG. 2 is a schematic representation of the tmovs ligand 20 (prior art). The difference between tmvs ligand 20 and tmvs ligand 10 of FIG. 1 is in the addition of three oxygen atoms to the three methyl groups to form three methoxy groups bound to the silicon atom. It is believed that the oxygen atoms of tmovs ligand 20 allow ligand 20 to more readily donate electrons to the Cu(hfac) complex, and so, allow tmovs ligand 20 to more tightly bind itself to Cu(hfac). There exist a variety of models to explain the bonding between the double bond carbon atoms and the Cu atom, and the quantitative bonding process is not entirely understood. The higher molecular weight of the three additional oxygen atoms will typically result in higher vaporization temperatures. An increase in the vaporization temperature of the precursor, without a corresponding increase in temperature stability, results in a precursor with inconsistent Cu decomposition characteristics that, in turn, cause Cu deposition problems. The present invention was invented in response to the need for a more temperature stable Cu precursor with a molecular weight less than tmovs ligand 20.

Figure 3:
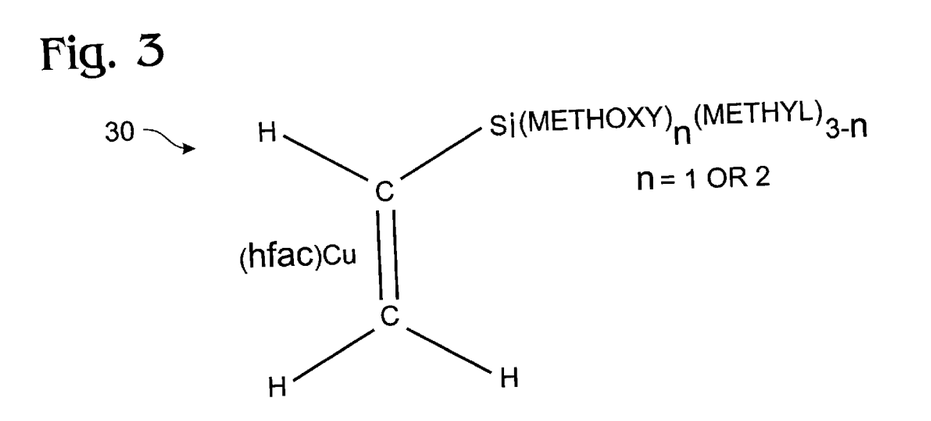
FIG. 3 is a schematic representation of the volatile Cu precursor compound of the present invention for the chemical vapor deposition (CVD) of Cu to selected surfaces.

The present invention was invented to bridge the gap between ligand 10 with three methyl groups ($CH_3$) and ligand 20 with three methoxy groups ($OCH_3$). FIG. 3 is a schematic representation of the volatile Cu precursor compound 30 of the present invention for the chemical vapor deposition (CVD) of Cu to selected surfaces. Precursor compound 30 comprises $Cu^{+1}(hfac)$, and a (methoxy)(methyl)silylolefin ligand. The ligand includes at least one methoxy group bonded to the silicon atom. The electron donation capability of the oxygen in the (methoxy)(methyl) silylolefin ligand provides a secure bond between the Cu and the (methoxy)(methyl)silylolefin ligand as the compound is heated to vaporization temperature.

Figure 4:
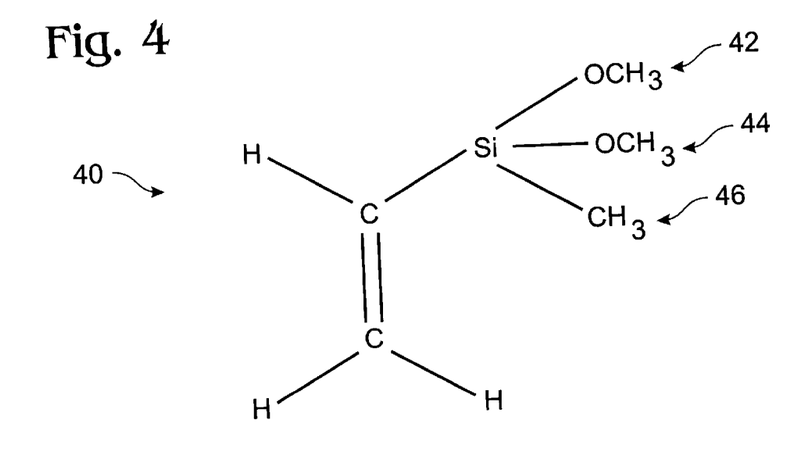
FIG. 4 is a schematic representation of an embodiment of the (methoxy)(methyl)silylolefin ligand of FIG. 3, where the ligand is a dimethoxymethylvinylsilane (dmomvs) ligand.
Figure 5:
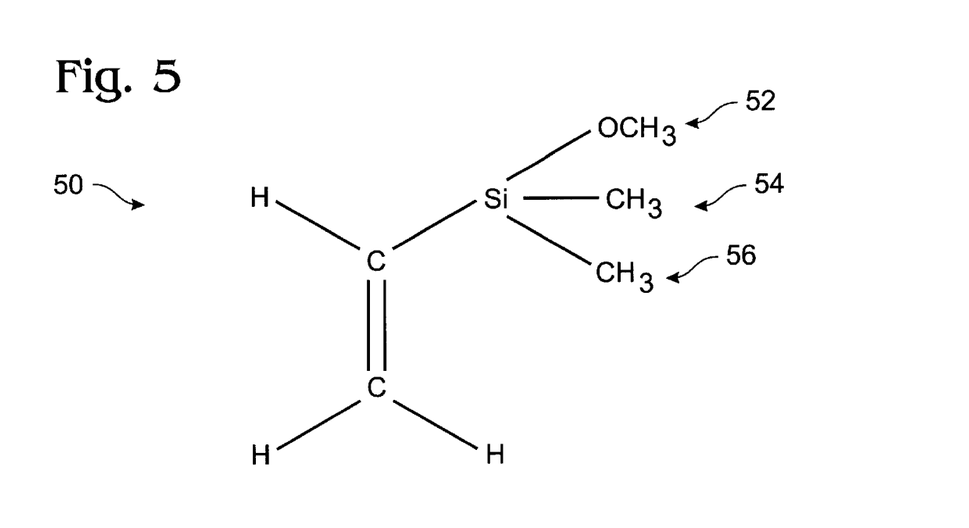
FIG. 5 is a schematic representation of another embodiment of the (methoxy)(methyl)silylolefin ligand of FIG. 3, where the ligand is a methoxydimethylvinylsilane (modmvs) ligand.

FIG. 4 is a schematic representation of an embodiment of the (methoxy)(methyl)silylolefin ligand of FIG. 3, where the ligand is a dimethoxymethylvinylsilane (dmomvs) ligand 40. The ligand includes two methoxy groups 42 and 44 ($OCH_3$), and one methyl group 46 ($CH_3$). The two oxygen atoms of the dimethoxymethyl group donate electrons to Cu to increase the temperature stability of the precursor. FIG. 5 is a schematic representation of another embodiment of the (methoxy)(methyl)silylolefin ligand of FIG. 3, where the ligand is a methoxydimethylvinylsilane (modmvs) ligand 50. The ligand includes one methoxy group 52 and two methyl groups 54 and 56. The single oxygen atom of the methoxydimethyl group minimally suppresses the precursor volatility.

Alternately, volatile copper (Cu) precursor compound 30 of FIG. 3 is represented by the following structural formula:

(hfac)Cu(H$_2$C=C(H)SiX$_3$)

in which each X group is selected from methyl ($CH_3$) and methoxy ($OCH_3$) groups, with at least one X group being methyl, and at least one X group being methoxy, whereby the electron donation capability of the oxygen in the methoxy group provides a secure bond between the Cu and the $H_2C$=$C(H)SiX_3$ ligand, as the compound is heated to vaporization temperature.

Alternately, dmomvs ligand 40 of FIG. 4 is represented in the format of the above structural formula when the X groups are two methoxy groups and one methyl group, whereby the two oxygen atoms of the methoxy groups donate electrons to Cu to increase temperature stability of the precursor. Likewise, modmvs ligand 50 of FIG. 5 is represented in the format of the above structural formula when the X groups are one methoxy group and two methyl groups, whereby the molecular weight of the methoxy group oxygen atom minimally suppresses the precursor volatility.

Figure 6:
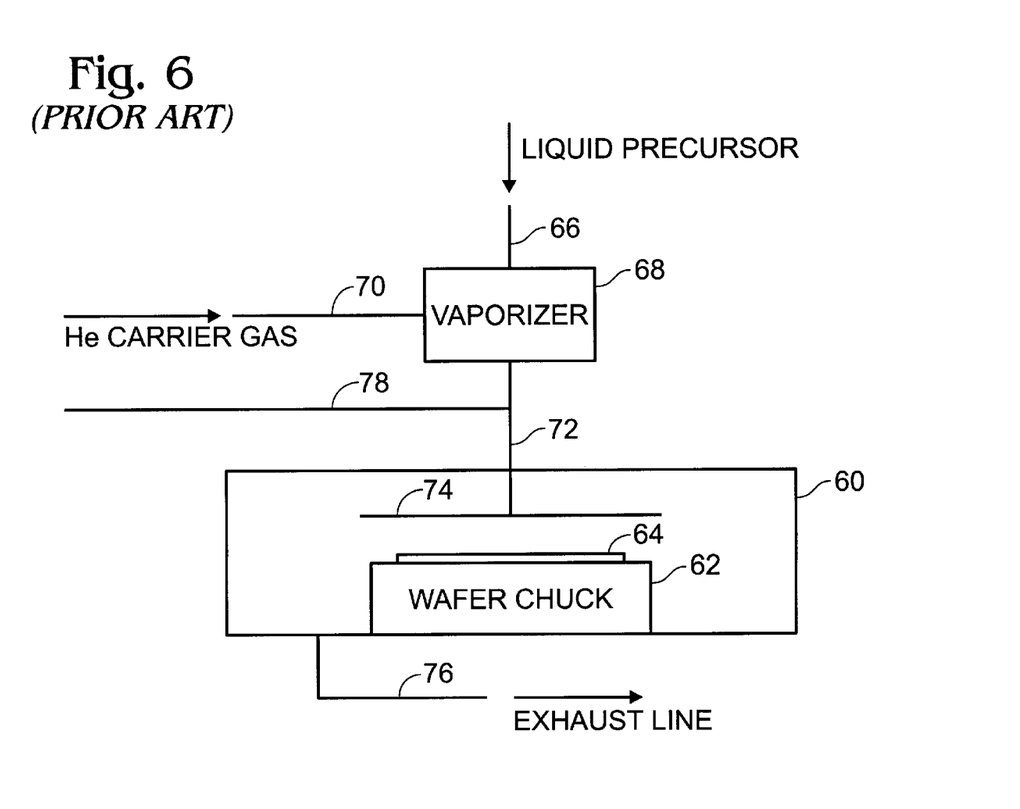
FIG. 6 is a block diagram of apparatus suitable to deposit Cu, with the precursor of the present invention, to selected surfaces.

FIG. 6 is a block diagram of apparatus suitable to deposit Cu, with the precursor of the present invention, to selected surfaces (prior art). An environmental chamber 60 is capable of maintaining a pressurized environment. Inside chamber 60 is a wafer chuck 62, and upon wafer chuck 62 is an IC, or wafer, having a selected surface 64. Cu precursor, in its liquid form, is introduced into line 66, and then into vaporizer 68, where the precursor is heated until it is volatile. Helium, or some other inert carrier gas, is introduced into line 70, and then into vaporizer 68, where it is mixed with the volatile precursor. The volatile precursor and carrier gas are carried through a line 72 to chamber 60. Inside chamber 60 the precursor/carrier gas mixture is dispersed through a showerhead 74, or some other equivalent gas dispersal means. Exhaust gases exit chamber 60 through a line 76. Line 76 is connected to a pump (not shown) to maintain a predetermined vacuum pressure in chamber 60.

Line 78 is used to introduce additives to the volatile precursor, typically the additives are in a volatile or gaseous form. In the preferred embodiment of the invention, the precursor compound in line 72 includes an additive from line 78 to create a precursor blend. The precursor blend introduced to chamber 60 further comprises water vapor having a vacuum partial pressure. The partial pressure is the percentage of the precursor/carrier/water blend in line 72 that is a result of pressure of the water vapor. The water vapor is blended with the precursor in line 72 so that the partial pressure of the water vapor is generally in the range of 0.5 to 5% of the precursor partial pressure. The precursor partial pressure is the percentage of the precursor blend pressure in line 72 that is a result of the pressure of the volatile precursor. The addition of water vapor to the precursor increases the rate of Cu deposition and the electrical conductivity of the deposited Cu. Alternately, additives are pre-packaged in the liquid precursor, or mixed with the liquid precursor compound in line 66.

As disclosed in co-pending application Ser. No. 08/745, 562, filed Nov. 8, 1996, entitled "Cu(hfac)TMVS Precursor With Water Additive To Increase The Conductivity Of Cu And Method For Same", invented by Nguyen et al., Attorney Docket No. SMT 244, the addition of water to a Cu(hfac) precursor, in the proper amounts, increases the deposition rate and the electrical conductivity of the deposited Cu.

The Cu precursor in line 66 is vaporized, in vaporizer 68, at a temperature generally in the range between 40° C. and 80° C. The Cu precursor in line 72 is applied, through showerhead 74, to each selected surface 64 at a temperature generally in the range between 40° C. and 80° C. The Cu precursor is delivered in line 72 to each selected surface 64 with an inert gas. The inert gas, introduced in line 70, has a vacuum partial pressure generally in the range of 50% to 1000% of the precursor partial pressure.

Other materials are added to the Cu precursor compound in either its liquid form in line 66, or in a vapor form on line 78, to enhance particular characteristics of the precursor. In one embodiment, the compound includes an additive to create a precursor blend, with the precursor blend further comprising less than approximately 5% hexafluoroacetylacetone (H-hfac), as measured by weight ratio of the precursor compound. The H-hfac additive facilitates a Cu disproportionation reaction which enhances the Cu deposition rate. The disproportionation reaction causes the $(hfac)^{-1}Cu^{+1}$ to reconfigure the Cu atoms into either $Cu^{+0}$ or $Cu^{+2}$ atoms. The uncharged Cu atoms become deposited on the selected surface, as an $(hfac)_2Cu^{+2}$ complex and the ligand exit the process as exhaust gases in line 76.

In another embodiment, the precursor compound includes an additive to create a precursor blend, in which the precursor blend further comprises less than approximately 10% silylolefins, as measured by weight ratio of the precursor compound. The silylolefins are added to prevent the Cu from prematurely decomposing as the precursor is heated. The additional silylolefins help stabilize the precursor, if the ligand prematurely cleaves, by forming bonds with (hfac) Cu. The silylolefins are selected from the group consisting of trimethylvinylsilane (tmvs), dmomvs, modmvs, trimethoxyvinylsilane (tmovs), triethoxyvinylsilane (teovs), ethoxymethoxymethylvinylsilane (eomomvs), diethoxymethylvinylsilane (deomvs), diethoxymethoxyvinylsilane (deomovs), ethoxydimethylvinylsilane (eodmvs), and ethoxydimethoxyvinylsilane (eodmovs).

Alternately, the Cu precursor compound includes an additive to create a precursor blend, with the blend including silylolefins having the following structural formula:

$$H_2C=C(H)SiX_3$$

in which each X group is selected from C1 through C8 alkyloxy groups and C1 through C8 alkyl groups. That is, the X groups may be all alkyloxy groups, all alkyl groups, or combinations of both. The possible alkyl groups include methyl (C1), ethyl (C2), propyl (C3), butyl (C4), pentyl (C5), hexyl (C6), heptyl (C7), or octyl (C8) groups, or combinations of these alkyl groups. Likewise, the possible alkyloxy groups include methoxy (C1), ethoxy (C2), propoxy (C3), butoxy (C4), pentyloxy (C5), hexyloxy (C6), heptyloxy (C7), or octyloxy (C8) groups, or combinations of these alkyloxy groups. Further, both alkyl and alkyloxy groups are selected from unsaturated and saturated chains of straight and branched carbon atoms, from saturated and unsaturated cyclic carbon arrangements, as is well known in the art.

In one embodiment, the precursor compound includes an additive to create a precursor blend, the blend further comprises less than approximately 5% H-hfac.$2H_2O$ (H-hfac dihydrate), as measured by weight ratio of the precursor compound, to increase the deposition rate of Cu. As noted above, the addition of water to the precursor generally increases the deposition rate of Cu on a selected surface.

In one embodiment, the precursor compound includes an additive to create a precursor blend, the blend further comprises less than approximately 0.4% H-hfac.$2H_2O$, as measured by weight ratio of the precursor compound, and less than approximately 5% silylolefins, as measured by weight ratio of the precursor compound. The water additive increases the deposition rate of Cu, and increases the electrical conductivity of the deposited Cu. The additional silylolefins help stabilize the precursor as it is heated.

Figure 7:
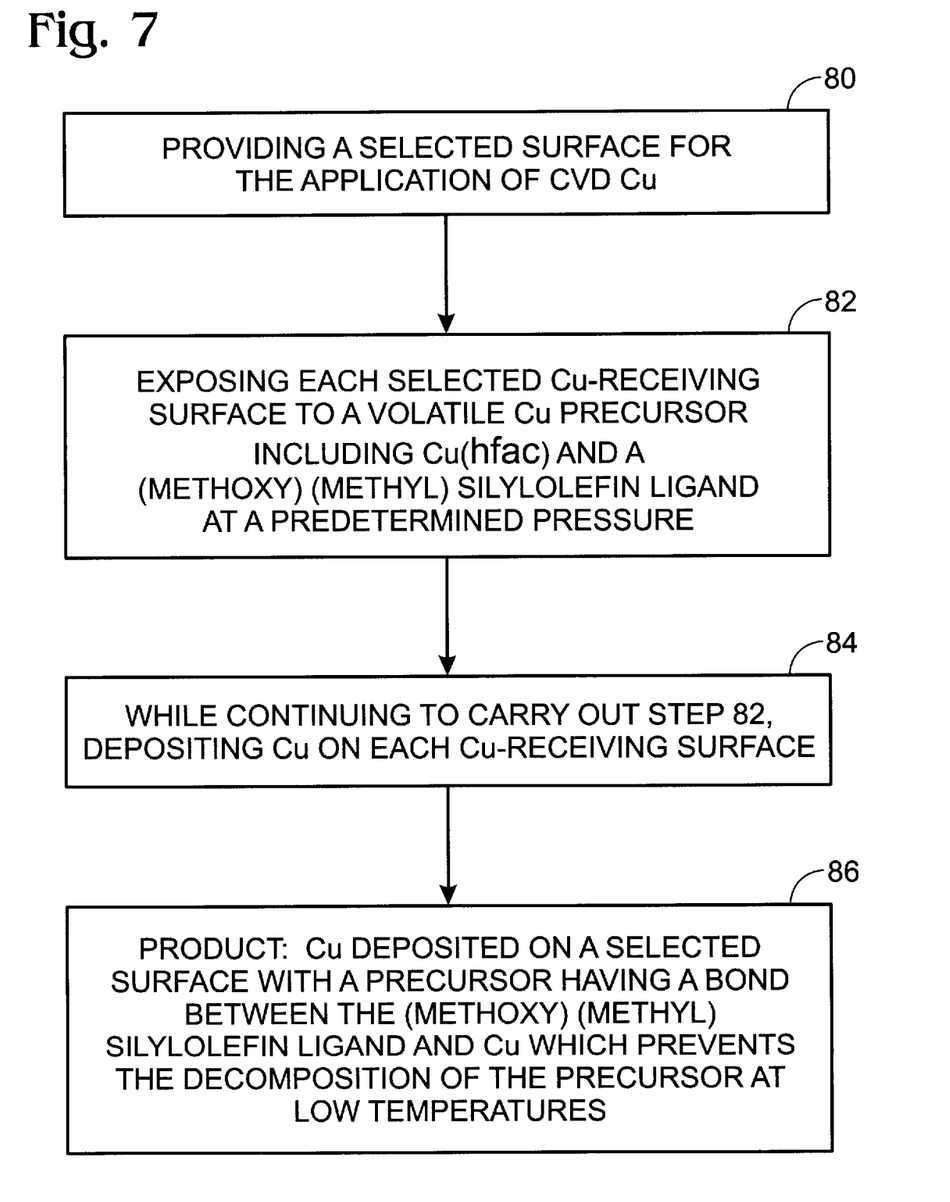
FIG. 7 illustrates steps in the method of applying CVD Cu on a selected surface.

FIG. 7 illustrates steps in the method of applying CVD Cu on a selected surface. Step 80 provides a selected surface for the application of CVD Cu. Step 82 exposes each selected Cu-receiving surface to a volatile Cu precursor compound including $Cu^{+1}$(hexafluoroacetylacetonate) and a (methoxy)(methyl)silylolefin ligand at a predetermined vacuum pressure. Step 84, while continuing to carry out Step 82, deposits Cu on each Cu-receiving surface. Step 86 is a product, Cu deposited on a selected surface with a precursor having a the bond between the (methoxy)(methyl)silylolefin ligand and Cu which prevents the decomposition of the precursor at low temperatures.

The preferred embodiment includes the further Step of, simultaneously with Step 82, exposing each selected Cu-receiving surface to water vapor at a vacuum partial pressure generally in the range between 0.5 and 5% of the precursor partial pressure. The addition of water vapor to the precursor increases the rate of Cu deposition and the electrical conductivity of the deposited Cu.

The Cu-receiving, or selected surface, of the above method is equivalent to selected surface 64 in FIG. 6. Each Cu-receiving surface in Step 84 has a temperature generally in the range between 160 and 250° C. It is the relatively high temperature of the target surface that preferably causes the Cu precursor to decompose, and so deposit uncharged Cu atoms on the surface. Cu is deposited on each Cu-receiving surface in Step 84 for a time generally in the range between 100 and 1000 seconds. That is, the controlled deposition process occurs within 100 to 1000 seconds.

The Cu precursor of the present invention is prepared in accord with methods suggested by prior art synthesis methods. For example, a suitable synthesis method is based on an approach taken by Doyle et al., in "Alkene and Carbon Monoxide Derivatives of Copper (I) and Silver (I) β-Diketonates", Organometallics, 1985, 4, pp. 830–835. The Cu precursor is obtained through the following reaction:

$$Cu_2O+2\ H\text{-hfac}+2\ L \rightarrow 2\ (hfac)CuL+H_2O$$

where L is the ligand dmomvs or modmvs. Another suitable synthesis method is suggested by Norman et al., in U.S. Pat. No. 5,085,731. In this method the precursor is obtained, using NaH instead of KH, through the following two step reaction:

$$NaH+H\text{-hfac} \rightarrow Na\text{-hfac}+H_2$$

$$CuCl+Na\text{-hfac}+L \rightarrow (hfac)CuL+NaCl$$

where, once again, L is either the dmomvs or modmvs silylolefin ligand.

Table 1 is a chart listing comparing the deposited thickness conductivities, and the efficiencies of Cu deposited using four different precursors. The precursors are as follows:

1) the original "Cupra Select" formula, a trademark of Schumacher, Carlsbad, Calif. 92009, or (hfac)Cu(tmvs);
2) (hfac)Cu(tmvs) with additives;
3) (hfac)Cu(tmvs) with water vapor per the method suggested in co-pending application Ser. No. 08/745,562, filed Nov. 8, 1996, entitled "Cu(hfac)TMVS Precursor With Water Additive To Increase The Conductivity Of Cu And Method For Same", invented by Nguyen et al., Attorney Docket No. SMT 244; and 4) the precursor of the present invention using the (hfac) Cu(dmomvs) compound with additional water vapor as suggested in the above mentioned application filed Nov. 8, 1996.

|  | Thickness | Deposit Time | Resistivity | Efficiency |
|---|---|---|---|---|
| (hfac)Cu(tmvs) | ≈900Å | 700 seconds | >100μ-ohm-cm | 1–5% |
| (hfac)Cu(tmvs) + Water | ≈3000Å | 250 seconds | ≈1.8μ-ohm-cm | 10–20% |
| Precursor of Present Invention + Water | 8029Å | 500 seconds | 2.02μ-ohm-cm | 13.20% |

TABLE 1

The various precursors were applied by the processes and apparatus generally depicted by FIG. 6. With respect to the precursor of the The various precursors were applied by the processes and apparatus generally depicted by FIG. 6. With respect to the precursor of the present invention, the total environmental pressure of chamber 60 was approximately 0.2T (Torr). The precursor flow in line 66 was approximately 0.5 cc/min, and the flow rate of the He gas in line 70 was approximately 100 cc/min. The temperature of vaporizer 68 was approximately 70° C. Selected surface 64 was a Si substrate covered with 2000 Å of TEOS oxide, which in turn, was covered with 500 Å of TiN. The temperature of the selected surface was approximately 195° C. The length of the deposition was optimized for the precursor used, generally between 250 and 700 seconds. The results show the precursor of the present invention is able to provide a substantially thicker deposition of Cu than the other methods, while providing comparable resistivity and efficiencies. Even better results are likely to be obtained after refinements in the process.

The precursor of the present invention bridges the gap between the prior art (hfac)Cu(tmvs) precursors that exhibit problems with premature decomposition and limited shelf life, and more recent precursors that offer increased temperature stability at the price of higher molecular weight. The present invention offers ligands comprised of either a single methoxy group having one oxygen atom to donate electrons to bond with Cu, or two methoxy groups with two oxygen atoms. The characteristics of the two ligands are utilized in specific situations, depending on the production environment, surface geometries, or process techniques that require differences in vaporization temperature and volatile precursor vacuum pressures.

Alternate embodiments of the precursor permit it to be blended with water, silylolefins, H-hfac, and combinations of additives to enhance deposition rates, Cu conductivity, and to minimize premature decomposition. These additives are blended with the precursor in either its liquid or volatile state Other embodiments of the invention will occur to those skilled in the art.

What is claimed is:

1. A volatile copper (Cu) precursor compound for the chemical vapor deposition (CVD) of Cu to selected surfaces, the precursor compound comprising:

$Cu^{+1}$(hexafluoroacetylacetonate); and a (methoxy)(methyl)silylolefin ligand, whereby the electron donation capability of the oxygen in said (methoxy)(methyl)silylolefin ligand provides a secure bond between the Cu and said (methoxy)(methyl) silylolefin ligand as the compound is heated to vaporization temperature.

2. A Cu precursor as in claim 1 in which said (methoxy)(methyl)silylolefin ligand is a dimethoxymethylvinylsilane (dmomvs) ligand, whereby the two oxygen atoms of the dimethoxymethyl group donate electrons to Cu to increase the temperature stability of the precursor.

3. A Cu precursor as in claim 1 in which said (methoxy)(methyl)silylolefin ligand is a methoxydimethylvinylsilane (modmvs) ligand, whereby the single oxygen atom of the methoxydimethyl group minimally suppresses the precursor volatility.

4. A Cu precursor as in claim 1 wherein the compound includes an additive to create a precursor blend, the precursor blend further comprising:

water vapor having a vacuum partial pressure, said water vapor blended with the precursor so that the partial pressure of said water vapor is generally in the range of 0.5 to 5% of the precursor partial pressure, whereby the addition of said water vapor to the precursor increases the rate of Cu deposition and the electrical conductivity of the deposited Cu.

5. A Cu precursor as in claim 1 in which the Cu precursor is vaporized at a temperature generally in the range between 40° C. and 80° C.

6. A Cu precursor as in claim 1 wherein the Cu precursor vapor is applied to each selected surface at a temperature generally in the range between 40° C. and 80° C.

7. A Cu precursor as in claim 1 wherein the precursor is delivered to each selected surface with an inert gas, and in which said inert gas has a vacuum partial pressure generally in the range of 50% to 1000% of the precursor partial pressure.

8. A Cu precursor as in claim 1 wherein the compound includes an additive to create a precursor blend, and in which the precursor blend further comprises:

less than approximately 5% hexafluoroacetylacetone (H-hfac), as measured by weight ratio of the precursor compound, to facilitate a Cu disproportionation reaction which enhances the Cu deposition rate.

9. A Cu precursor as in claim 1 wherein the compound includes an additive to create a precursor blend, and in which the precursor blend further comprises:

less than approximately 10% silylolefins, as measured by weight ratio of the precursor compound, to prevent said Cu from prematurely decomposing as the precursor is heated.

10. A Cu precursor as in claim 9 in which said silylolefins are selected from the group consisting of trimethylvinylsilane (tmvs), dimethoxymethylvinylsilane (dmomvs), methoxydimethylvinylsilane (modmvs), trimethoxyvinylsilane (tmovs), trimethoxyvinylsilane (teovs), ethoxymethoxymethylvinylsilane (eomomvs), diethoxymethylvinylsilane (deomvs), diethoxymethoxyvinylsilane (deomovs), ethoxydimethylvinylsilane (eodmvs), and ethoxydimethoxyvinylsilane (eodmovs).

11. A Cu precursor as in claim 1 wherein the compound includes an additive to create a precursor blend, and in which the blend further comprises:

less than approximately 5% H-hfac.$2H_2O$, as measured by weight ratio of the precursor compound, to increase the deposition rate of Cu.

12. A Cu precursor as in claim 1 wherein the compound includes an additive to create a precursor blend, and in which the blend further comprises:

less than approximately 0.4% H-hfac.$2H_2O$, as measured by weight ratio of the precursor compound; and less than approximately 5% silylolefins, as measured by weight ratio of the precursor compound, to increase the deposition rate of Cu, and to increase the electrical conductivity of the deposited Cu.

13. A method for applying chemical vapor deposition (CVD) copper (Cu) on a selected surface, the method comprising the steps of:

a) exposing each selected Cu-receiving surface to a volatile Cu precursor compound including $Cu^{+1}$ (hexafluoroacetylacetonate) and a (methoxy)(methyl) silylolefin ligand at a predetermined vacuum pressure; and b) while continuing to carry out step a), depositing Cu on each Cu-receiving surface, whereby the bond between the (methoxy)(methyl)silylolefin ligand and Cu prevents the decomposition of the precursor at low temperatures.

14. A method as in claim 13 in which the (methoxy)(methyl)silylolefin ligand is a dimethoxymethylvinylsilane (dmomvs) ligand, whereby the two oxygen atoms of the dimethoxymethyl group donate electrons to Cu to increase the temperature stability of the precursor.

15. A method as in claim 13 in which the (methoxy)(methyl)silylolefin ligand is methoxydimethylvinylsilane (modmvs) ligand, whereby the single oxygen atom of the methoxydimethyl group minimally suppresses the precursor volatility.

16. A method as in claim 13 including the further step of:

c) simultaneously with step a), exposing each selected Cu-receiving surface to water vapor at a vacuum partial pressure generally in the range between 0.5 and 5% of the precursor partial pressure, whereby the addition of water vapor to the precursor increases the rate of Cu deposition and the electrical conductivity of the deposited Cu.

17. A method as in claim 13 in which each Cu-receiving surface in step b) has a temperature generally in the range between 160 and 250° C.

18. A method as in claim 13 in which the precursor vaporization temperature in step a) is generally in the range between 40° C. and 80° C.

19. A method as in claim 13 in which Cu is deposited on each Cu-receiving surface in step b) for a time generally in the range between 100 and 1000 seconds.

20. A method as in claim 13 in which step a) includes applying the Cu precursor vapor to each selected surface at a temperature generally in the range between 40° C. and 80° C.

21. A method as in claim 13 in which step a) includes delivering the Cu precursor to each selected surface with an inert gas, in which the inert gas has a vacuum partial pressure generally in the range of 50 to 1000% of the precursor partial pressure.

22. A method as in claim 13 in which step a) includes adding less than approximately 5% H-hfac, as measured by weight ratio of the precursor compound, to the precursor compound to create a precursor blend, whereby the H-hfac facilitates a Cu disproportionation reaction which enhances the Cu deposition rate.

23. A method as in claim 13 in which step a) includes adding less than approximately 10% silylolefins, as measured by weight ratio of the precursor compound, to the precursor compound to create a precursor blend, whereby the silylolefins prevent the Cu from prematurely decomposing as the precursor is heated.

24. A method as in claim 13 in which the silylolefin is selected from the group consisting of tmvs, dmomvs, modmvs, tmovs, teovs, eomomvs, deomvs, deomovs, eodmvs, and eodmovs.

25. A method as in claim 13 in which step a) includes adding less than approximately 5% $H\text{-}hfac.2H_2O$, as measured by weight ratio of the precursor compound, to the precursor compound to create a precursor blend to increase the deposition rate of Cu.

26. A method as in claim 13 in which step a) includes adding less than approximately 0.4% $H\text{-}hfac.2H_2O$ and less than approximately 5% silylolefins, as measured by weight ratio of the precursor compound, to the precursor compound to create a precursor blend, thereby increasing the deposition rate of Cu, increasing the electrical conductivity of the deposited Cu.

27. A volatile copper (Cu) precursor compound for applying chemical vapor deposition (CVD) copper (Cu) to selected surfaces, the precursor compound being represented by the structural formula:

in which each X group is selected from methyl ($CH_3$) and methoxy ($OCH_3$) groups, with at least one said X group being methyl, and at least one said X group being methoxy, whereby the electron donation capability of the oxygen in said methoxy group provides a secure bond between the Cu and said ($H_2C\!=\!C(H)SiX_3$) ligand, as the compound is heated to vaporization temperature.

28. A Cu precursor as in claim 27 in which said X groups are two methoxy groups and one methyl group, whereby the two oxygen atoms of the methoxy groups donate electrons to Cu to increase temperature stability of the precursor.

29. A Cu precursor as in claim 27 in which said X groups are one methoxy group and two methyl groups, whereby the molecular weight of the methoxy group oxygen atom minimally suppresses the precursor volatility.

30. A Cu precursor as in claim 27 in which the compound includes an additive to create a Cu precursor blend, the blend further comprising silylolefins having the following structural formula:

in which each said X group is selected from C1–C8 alkyloxy groups and C1–C8 alkyl groups.

* * * * *